United States Patent [19]

van Sorge

[11] 4,201,880

[45] May 6, 1980

[54] PREPARATION OF ORTHO-ALKYLATED PHENOLS

[75] Inventor: Bernardus J. van Sorge, Selkirk, N.Y.

[73] Assignee: General Electric Company, Pittsfield, Mass.

[21] Appl. No.: 879,768

[22] Filed: Feb. 21, 1978

Related U.S. Application Data

[62] Division of Ser. No. 651,251, Jan. 22, 1976, Pat. No. 4,097,411.

[51] Int. Cl.² ..................... C07C 37/12; C07C 39/06
[52] U.S. Cl. .................................................. 568/804
[58] Field of Search ........................................ 568/804

[56] References Cited

U.S. PATENT DOCUMENTS

| | | | |
|---|---|---|---|
| 3,446,856 | 5/1969 | Hamilton | 568/804 |
| 3,968,172 | 7/1976 | Ichikawa et al. | 568/804 |
| 3,971,832 | 7/1976 | Watanabe et al. | |

*Primary Examiner*—Werren B. Lone
*Attorney, Agent, or Firm*—Morgan, Finnegan, Pine, Foley & Lee

[57] ABSTRACT

This invention is for a shaped, alkylation catalyst comprising magnesium oxide bonded with silica and to the use of the catalyst in a process for the ortho-alkylation of phenols. The process comprises the vapor phase reaction of a non-ortho-substituted phenol with an alcohol in the presence of a catalyst. The catalyst of the invention is an improvement over prior art catalysts used for ortho-alkylation of phenols as it substantially increases reaction selectivity, eliminates loss of catalyst arising with the use of powders or weakly sintered composites and has a substantially extended useful life.

10 Claims, No Drawings

PREPARATION OF ORTHO-ALKYLATED PHENOLS

This is a division of application Ser. No. 651,251 filed Jan. 22, 1976, now U.S. Pat. No. 4,097,411.

BACKGROUND OF THE INVENTION

1. Introduction

This invention relates to the ortho-alkylation of phenols, and more particularly, to the vapor-phase orthoalkylation of phenols by reaction of a non-ortho-alkylated phenol with an alcohol in the presence of a shaped catalyst comprising magnesium oxide bonded with silica.

2. Description of the Prior Art

In commonly assigned Hamilton U.S. Patent Application Ser. No. 371,189, filed May 29, 1964, there is disclosed and claimed a method for methylating the ortho positions of phenols by the vapor phase reaction of a phenol with methanol in the presence of magnesium oxide as a catalyst at a catalyst bed temperature in a range of 475° to 600° C. Under the conditions described in the Hamilton application, phenol is selectivity ortho-methylated in yields in excess of 95%. Thus, the reaction offers a means for economically converting phenol to orthocresol, a useful disinfectant and wood preservative, and for converting both phenol and ortho-cresol to 2,6-xylenol, a monomer which can be polymerized to form poly-2,6-xylenol, a high performance thermoplastic material.

While the Hamilton invention provides an economic synthesis for both 2,6-xylenol and also ortho-cresol from phenol, the service life of the magnesium oxide catalyst is relatively short due to the high temperature at which the reaction is required to take place—i.e. about 75 to 100 hours service life at the typical reaction temperature of about 530° C. Also, the magnesium oxide catalyst of the Hamilton application is only moderately selective with respect to methanol with methanol selectivity being in the range of about 40 to 50%. This means that more than about two moles of methanol are required for each mole of phenol entering into reaction with the methanol. In addition, use of unmodified magnesium oxide in powdered or weakly sintered form results in a rather large induction period for maximum selectivity. The term "induction period" may be defined as the period from the time of starting the reaction to the time at which the catalyst reaches and maintains maximum ortho-alkylation selectivity. Finally, the use of magnesium oxide in powdered or sintered form provides numerous processing difficulties.

Statement of the Invention

The present invention is predicated upon the discovery that if the ortho-alkylation catalyst consists of magnesium oxide bonded with silica, the alkylation reaction will proceed with a high degree of both methanol and phenol selectivity and the induction period of maximum selectivity is reduced. Moreover, the catalyst may be molded to a desired shape and will have strength properties that will prevent particles of the catalyst from breaking or flaking off in operation or handling thereby substantially extending the service life of the catalyst with a minimum of loss during operation. In addition, the reaction temperature may be reduced thereby improving the overall economy of the process.

Accordingly, the present invention has as one objective, the provision of a catalyst which will enable orthoalkylation of phenol to be carried out with a high degree of selectivity and high yield.

Another objective of the invention is to provide a magnesium oxide catalyst having excellent physical strength properties which may be molded to a desired shape and which will have a service life of many of hundreds of hours before needing regeneration or other treatment.

Still another object of the invention is to provide a process for formation of ortho-alkylated phenols in high yield.

Description of the Preferred Embodiments

In one aspect, the ortho-alkylation catalyst of the invention is provided by blending finely divided magnesium oxide powders with finely divided silica. The powders of both the magnesium oxide and silica are preferably maintained below an average particle size of 500 microns in diameter. The concentration of silica is preferably maintained low and may be as little as 1% by weight or as high as 15% or more. The preferred range varies from 2 to 6% by weight. After the powders are blended, water is added to the blend in an amount sufficient to wet the blend so that it may be molded to shape. Typically, one part by weight water is added to each part of the powder blend. The blend is then molded to shape under pressure and dried at about 200° F. and subsequently calcined at an elevated temperature for a time sufficient to dry the catalyst. In general, the calcination temperature may vary between 400 and 850° F. for a period of up to 3 hours, but lower calcination temperatures are preferred, 300° to 500° F. being most preferred. As water is evaporated from the catalyst, minute pores form thereby exposing the magnesium oxide and making the catalyst active. A surface area of at least 20, and preferably from 130 to 200 sq. meters per gram of catalyst is desirable. The shape of the catalyst may be in the form of Raschig rings, cylinders, tablets or any other shape known to the art.

The method for forming the ortho-alkylated phenols comprises a vapor-phase reaction of an alkyl alcohol and a nonortho-substituted phenol in the presence of the catalyst of this invention at a catalyst bed temperature of at least 460° C. and preferably at a temperature varying between 460° C. and 500° C. In general, the process is similar to the process disclosed in the above-noted Hamilton Application Ser. No. 371,189 and differs therefrom by the substitution of the catalyst of this invention and somewhat lower reaction temperatures.

While the invention has been described as applying specifically to phenol and ortho-cresol, it applies in general to phenols having an ortho-hydrogen. For example, it also applies to ortho-phenyl phenol, ortho-ethyl phenol and to phenols in which there are alkyl and aryl groups on the metaand para- positions. These phenols may be represented by the formula

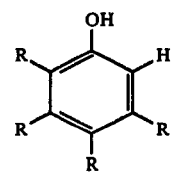

where each R is a monovalent substituents selected from the group consisting of hydrogen, lower alkyl, phenyl, and lower alkyl substituted phenyl.

The magnesium oxide used as catalyst in conjunction with the silica binder is a material having a very high surface to weight ratio. Magnesium oxides having the desired porosity may be prepared by thermally decomposing magnesium carbonate, basic magnesium carbonate, and magnesium hydroxide as these materials may be converted to magnesium oxide without fusing or sintering.

In carrying out an alkylation in accordance with this invention, any one or a mixture of phenols having an orthohydrogen may be vaporized and passed through a reactor heated to a temperature of at least 460° C. containing the magnesium oxide catalyst of the invention. In order to obtain the maximum yield of ortho-alkylated products, at least one mole of an alkyl alcohol and preferably from 1 to 3 moles of the alcohol is used for each ortho position in the phenol to be alkylated. For example, if phenol which has two ortho-hydrogens per molecule is to be methylated to produce a maximum yield of 2,6-xylenol, it is desirable to use 2 to 6 moles of methanol for higher ratio of methanol to phenol.

The vapors issuing from the reactor are condensed and the products separated in conventional manner, such as by crystallization, distillation, etc. The reaction proceeds at atmospheric pressure, but it is obvious that pressures above or below atmospheric pressure may be used.

The selectivity favoring ortho-alkylation over meta or para-alkylation under steady state conditions is substantially the same for the magnesium oxide catalyst of the invention as for pure magnesium oxide. One advantage to operating with the catalyst of this invention resides in the fact that the life of the catalyst is substantially extended before regeneration or other treatment is needed. Catalysts made according to this invention have operated without substantial reduction in catalytic activity for periods of time in excess of 1,000 hours.

An additional advantage accruing to the magnesium oxide catalyst of the invention lies in the increase in the selectivity of the reactants, especially the selectivity of methanol. Using the magnesium oxide catalyst of the prior art under state conditions, the selectivity of methanol varies from about 40 to 50%. With the magnesium oxide catalyst of this invention using a silica binder, selectivity of methanol is increased to in excess of 65%.

In the following example 1, the system used to conduct the reaction consisted of a reservoir containing a solution of methanol and phenol connected to a metering pump which feeds the reactions through ¼" stainless steel tube into a vertical vaporizer made from a 12" long piece of 1" O. D., 0.8" I. D. stainless steel tubing. The vaporizer was partially immersed in a bath of fused salt to a depth of about 6". The vapors from the reactor were fed to a 0.8" I. D. stainless steel tube reactor through a 1" length of ¼" I. D. stainless steel pipe located 5½" above the bottom of the vaporizer and connected to the reactor 13" from its bottom. The reactor was 24" long and was immersed in the fused salt bath to a depth of about 14". Since the inlet tube of the reactor coming from the vaporizer also passed through the fused salt bath, it served as a preheater for the vapor issuing from the vaporizer to bring the vapor up to the temperature of the reactor. The reactor was equipped with a thermowell made from ⅛" stainless steel tubing concentrically located in the reactor and extending downward into the catalyst bed to a depth of 1" to 6". Thus, the catalyst bed temperature could be measured throughout a large section of the tube. The reactor tube was filled with a constant volume of 100 milliliters of catalyst which filled the tube to a depth of about 12". Thus, vapors were fed to the top of the catalyst bed in the reactor and product vapors left the reactor through a ⅜" O. D. stainless steel tube connected to the bottom of the reactor. The product vapors from the reactor were fed to a water-cooled condenser and receiver.

The catalyst used was prepared by blending 200 grams of commercial magnesium oxide catalyst with about 6 grams of silica powder, and about 200 grams of water. The blend was molded into cylindrically shaped pellets having a diameter and length of 3/16". The catalyst was dried at 200° F. and calcined by heating to about 450° F. for about three hours. The catalyst was then placed in a reaction chamber which was maintained at a temperature of 480° C. The feed composition was vaporized and the vapors passed through the catalyst chamber. The conditions and results are indicated in the following table:

TABLE 1

|  | Example 1 |
|---|---|
| Feed Composition |  |
| Molar Ratio Methanol to Phenol | 6:1 |
| Wt. % Water in Feed | 13 |
| Operating Conditions |  |
| Temperature (°C.) | 470 |
| LHSV (hr$^{-1}$)* | 2.2 |
| Pressure (psig) | 0 |
| Phenolic Distribution (wt. %) |  |
| 0-cresol | 25.9 |
| 2,6-xylenol | 51.0 |
| 2,4,6-mesitol | 4.4 |
| Phenol | 18.3 |

*LHSV is the liquid hourly space velocity and defines the volume of liquid per volume of catalyst per hour.

From the above table, it can be seen that the alkylation which took place was primarily in the ortho-position. The ortho-cresol formed in the reactor and unreacted phenol may be recycled if desired. By increasing the liquid hourly space velocity, the ratio of ortho-cresol to 2,6-xylenol may be substantially increased. For example, using substantially the same reaction conditions and an increase in the liquid hourly space velocity to 3.47 hrs$^{-1}$ would result in a phenolic distribution comprising about 42.7% unreacted phenol, 36.2% orthocresol, 20.2% 2,6-xylenol and 0.8% 2,4,6-mesitol.

In the following examples 2 and 3, the procedure of example 1 is repeated. In example 2, the catalyst used was substantially the same as that of example 1. In example 3, the catalyst used was prepared by pelletizing and calcining substantially pure powdered magnesium oxide at a temperature of about 500° F. The conditions and results are set forth in the following table:

TABLE 11

|  | Example 2 | Example 3 |
|---|---|---|
| Feed Composition |  |  |
| Molar Ratio Methanol to Phenol | 5:1 | 5:1 |
| Wt. % Water to Feed | 10 | 12.4 |
| Operating Conditions |  |  |
| Temperature (°C.) | 478 | 539 |
| LHSV (hr.$^{-1}$) | 1.44 | 1.65 |
| Pressure (psig) | 0 | 0 |
| Results |  |  |
| Molar Phenol Selectivity[1] | 92.0 | 89.5 |
| Molar Methanol Selectivity[2] | 85.4 | 59.5 |

TABLE 11-continued

|  | Example 2 | Example 3 |
| --- | --- | --- |
| Production Rate<br>(lbs/2,6-xylenol/hr./ft. catalyst) | 22.1 | 14.0 |
| Catalyst Life | 400 hours | 80 hours |

[1]The molar phenol selectivity is defined as the ratio of phenol converted to 2,6-xylenol to phenol converted to 2,6-xylenol and by-products multiplied by 100. The amount of phenol converted to ortho-cresol is not included in the definition as it is recycled in the feed stream if desired.

[2]The molar methanol selectivity is defined as the ratio of methanol reacted to form 2,6-xylenol to the methanol reacted to form 2,6-xylenol and other by-products multiplied by 100. The amount of methanol converted to ortho-cresol is not included in the definition as it is recycled in the feed stream if desired.

From the above table, it can be seen that the life of the catalyst of this invention is substantially increased over the prior art magnesium oxide catalyst. Moreover, methanol selectivity is substantially improved.

While the foregoing discloses certain specific embodiments of the invention, it is understood that there are many modifications which obviously fall within the proper scope of the invention. Accordingly, the invention is intended to be limited in scope only as may be necessitated by the scope of the appended claims:

I claim:

1. In a process for alkylating a phenol in the ortho position which comprises the vapor phase reaction in the presence of an alkylation catalyst of an alkyl alcohol and a phenol having the general formula

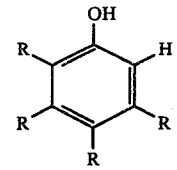

where R is a monovalent substituent selected from the group consisting of hydrogen, lower alkyl, phenyl, and lower alkyl substituted phenyl; the improvement comprising performing the reaction at a temperature of about about 460° C. in the presence of a molded to shape catalyst comprising a mixture of a magnesium oxide bonded with a minor amount of silica, the catalyst having a surface area of at least 20 square meters per gram and containing from about 1 to about 15% by weight of silica.

2. The process of claim 1 where the alkyl alcohol is methyl alcohol.

3. The process of claim 2 where the catalyst bed temperature is maintained at a temperature of at least 460° C.

4. The process of claim 2 where each R is hydrogen.

5. The process of claim 2 where the phenol is ortho-cresol.

6. The process of claim 2 where the phenol is a mixture of unsubstituted phenol and ortho-cresol.

7. The process of claim 2 where the silica comprises from 1 to 15% by weight of the total catalyst.

8. The process of claim 2 where the silica comprises from 2 to 6% by weight of the total catalyst.

9. The process of claim 1 wherein the catalyst is in the shape of pellets.

10. The process of claim 1 wherein the catalyst is in the shape of a Rashig ring.

* * * * *